United States Patent [19]

Blanchard et al.

[11] Patent Number: 5,332,855
[45] Date of Patent: Jul. 26, 1994

[54] AMMOXIDATION OF SATURATED HYDROCARBONS

[75] Inventors: Gilbert Blanchard, Belleville; Gilbert Ferre, Livry Gargan, both of France

[73] Assignee: Rhone-Poulenc Chimie, Courbevoie, France

[21] Appl. No.: 17,295

[22] Filed: Feb. 12, 1993

[30] Foreign Application Priority Data

Feb. 20, 1992 [FR] France .................. 92 02195

[51] Int. Cl.$^5$ ........................................ C07C 253/24
[52] U.S. Cl. .................................................. 558/319
[58] Field of Search ......................................... 558/319

[56] References Cited

U.S. PATENT DOCUMENTS

| | | | |
|---|---|---|---|
| 3,365,482 | 1/1968 | Khooblar | 558/319 |
| 3,395,159 | 7/1968 | Levine | 558/319 X |
| 3,433,823 | 3/1969 | McMahon | 558/319 |
| 3,670,009 | 6/1972 | Taylor | 558/319 |
| 3,678,090 | 7/1972 | Taylor | 558/319 |
| 3,686,267 | 8/1972 | Taylor | 558/319 |
| 3,746,737 | 7/1973 | Tulman | 558/319 |
| 3,833,638 | 9/1974 | Knox et al. | 558/319 |
| 3,927,007 | 12/1975 | Lüssling, et al. | 260/465 C X |
| 4,309,361 | 1/1982 | Suresh et al. | 558/319 X |
| 4,760,159 | 7/1988 | Suresh et al. | 558/319 |
| 4,767,739 | 8/1988 | Glaeser et al. | 502/209 |
| 4,783,545 | 11/1988 | Glaeser et al. | 558/319 |
| 4,801,568 | 1/1989 | Brazdil, Jr.; et al. | 502/209 |
| 4,801,727 | 1/1989 | Glaeser et al. | 558/319 |
| 4,814,478 | 3/1989 | Glaeser et al. | 558/319 |
| 4,866,024 | 9/1989 | Brazdil, Jr.; et al. | 502/209 |
| 4,871,706 | 10/1989 | Brazdil, Jr.; et al. | 558/319 X |
| 4,877,764 | 10/1989 | Glaeser et al. | 502/209 |
| 4,883,896 | 11/1989 | Glaeser et al. | . |
| 4,888,438 | 12/1989 | Glaeser et al. | 558/319 |
| 5,008,427 | 4/1991 | Brazdil, Jr.; et al. | 558/319 |

FOREIGN PATENT DOCUMENTS

| | | |
|---|---|---|
| 0282314 | 9/1988 | European Pat. Off. . |
| 0342777 | 11/1989 | European Pat. Off. . |
| 0344884 | 12/1989 | . |
| 2027238 | 9/1970 | France . |
| 2072334 | 9/1971 | France . |
| 2072399 | 9/1971 | France . |
| 2119492 | 8/1972 | France . |
| 2119493 | 8/1972 | France . |
| 1336135 | 11/1973 | United Kingdom . |
| 1336136 | 11/1973 | United Kingdom . |
| 1337759 | 11/1973 | United Kingdom . |

OTHER PUBLICATIONS

Kim, et al., Chemistry Letters, 1989, pp. 2173-2176.
Japanese Patent Abstract No. JP3058961, Application No. JP890191317, Published May 27, 1991, vol. 015206.
Arzu B. Azimov, et al, *Journal of Catalysis*, "Dehydrogenation" Mechanism for Ammoxidation of Alkylaromatic Hydrocarbons, vol. 127, pp. 354–365, (1991).

*Primary Examiner*—Joseph Paul Brust
*Attorney, Agent, or Firm*—Burns, Doane, Swecker & Mathis

[57] ABSTRACT

The alkanes, e.g., propane, are ammoxidized into admixtures containing $\alpha,\beta$-unsaturated nitriles, e.g., admixture of acrylonitrile and propylene, by reacting such alkane with ammonia and oxygen, in vapor phase, in the presence of a catalytically effective amount of a solid catalyst, at least one active catalytic phase of which having empirical formula (I):

$$VSb_aM_bO_x \qquad (I)$$

in which a is a whole or fractional number equal to or greater than 1, M is iron and/or gallium and/or indium, b is a whole or fractional number equal to or greater than 0.5, and x is a whole or fractional number provided by the oxidation number of the other elements of the at least one active catalytic phase.

22 Claims, 1 Drawing Sheet

AMMOXIDATION OF SATURATED HYDROCARBONS

CROSS-REFERENCE TO COMPANION APPLICATION

Our copending application Ser. No. 08/014,757, filed Feb. 8, 1993 and assigned to the assignee hereof.

BACKGROUND OF THE INVENTION

1. Field of the Invention:

The present invention relates to the ammoxidation of saturated hydrocarbons, and, more especially, to the ammoxidation/conversion of alkanes into a mixture containing $\alpha,\beta$-unsaturated nitriles.

2. Description of the Prior Art:

The ammoxidation of olefins and, in particular, of propylene, is well known to this art. However, although the saturated hydrocarbons, which are more widely available, are the more desirable starting materials from an economic standpoint, it is also well known to this art that they do not display comparable reactivity in this type of reaction to form, especially, $\alpha,\beta$-unsaturated nitriles.

One of the difficulties encountered in the ammoxidation of saturated hydrocarbons resides is the requirement for catalysts capable of dehydrogenating the saturated hydrocarbon under conditions which minimize or eliminate the combustion of the ammonia and/or that of the hydrocarbon, while at the same time ensuring a reasonable selectivity either for the $\alpha,\beta$-unsaturated nitrile (target compound), for example for acrylonitrile starting from propane, or for added value compounds (above-mentioned nitrile and olefin), for example, for acrylonitrile and propylene starting from propane.

U.S. Pat. No. 3,365,482 describes the ammoxidation, especially of isobutane into methacrylonitrile, on a molybdenum-based catalyst deposited onto eta-alumina, doped with antimony, at 508° C., starting from a gaseous mixture containing isobutane, air, ammonia and steam (1.0/4.5/1.0/12.5); the selectivity for methacrylonitrile attains a value of 49% for a degree of conversion of the isobutane of 22%.

When the starting material is a gaseous mixture of propane/air/ammonia/steam (1.0/4.7/0.67/12.8), using the same catalyst and at 550° C., the selectivity for acrylonitrile decreases to 15% for a degree of conversion of the propane of 29%.

In Chemistry Letters, pp. 2173-2176 (1989), the ammoxidation of propane in the vapor phase is described, in the presence of multicomponent metal oxides containing molybdenum and bismuth and having a structure of the type of that of scheelite. It appears that, despite the relatively moderate temperatures used, the proportion of combustion products (CO, CO$_2$) is very high in all instances (at least 15%) and that certain catalytic compositions tested exhibit very little activity with respect to the desired reaction, while being used under conditions which are in the explosive region or very near the explosive region.

It is immediately apparent that the coproduction of large amounts of CO and CO$_2$ is undesirable on an industrial scale.

In addition, the use of reaction mixtures which are in the explosive region, compositionally, is even less desirable on an industrial scale, since the process is used in a stationary bed.

U.S. Pat. No. 5,008,427 describes a process for the ammoxidation of propane or isobutane into an $\alpha,\beta$-unsaturated mononitrile, by reaction in the vapor phase with oxygen and ammonia, in the presence of a catalyst comprising vanadium, antimony, oxygen and titanium and/or tin and/or iron and/or chromium and/or gallium and, optionally, one or more other elements selected from among 23 very diverse metals. Other than the composition of the catalyst, the principal characteristics of such process are the calcination temperature of the catalyst, which must be at least 780° C., and the alkane/ammonia (from 2.5 to 16) and alkane/oxygen (from 1 to 10) molar ratios.

This process would thus permit obtaining good productivity in respect of unsaturated nitriles employing a catalyst which does not agglomerate.

However, this '427 patent, which is thus essentially oriented in the direction of particular operating conditions such as calcination temperature or reactant ratios, does not describe selected compositions containing an active phase which permits attaining a good selectivity for the unsaturated nitriles.

SUMMARY OF THE INVENTION

Accordingly, a major object of the present invention is the provision of an improved process for the appreciably selective ammoxidation of alkanes into admixture of added value compounds containing an $\alpha,\beta$-unsaturated nitrile, in particular acrylonitrile, while reducing the losses in starting material, especially by reason of the formation of oxides of carbon.

Another object of this invention is the provision of an improved process for the ammoxidation of alkanes in the presence of a solid catalyst that is relatively simple to prepare and active in the absence of halogenated promoter and effective in respect of gas mixtures which are not necessarily in the explosive region.

Briefly, the present invention features a process for the ammoxidation of alkanes in the vapor phase in the presence of a solid catalyst comprising at least one active phase, said at least one active phase having the following empirical formula (I):

$$VSb_aM_bO_x \quad\quad (I)$$

in which a is a whole or fractional number equal to or greater than 1, M is an iron and/or gallium and/or indium atom, b is a whole or fractional number equal to or greater than 0.5, and x is a whole or fractional number provided by the oxidation number of the other elements of said at least one active phase.

DETAILED DESCRIPTION OF PREFERRED EMBODIMENTS OF THE INVENTION

More particularly according to the present invention, in a preferred embodiment thereof, in the at least one active phase having the formula (I), a is a whole or fraction number of up to 20 and more preferably ranges from 1 to 10, and b is a whole or fractional number of up to 20 and more preferably ranges from 1 to 10.

Among the metals represented by M in the formula (I) of the at least one active phase, iron is generally preferred as this provides excellent selectivities in the preparation of unsaturated nitriles and ethylenically unsaturated hydrocarbons, while also exhibiting good activity.

According to the present invention, acyclic saturated hydrocarbons having from 3 to 12 carbon atoms per molecule are reacted in the vapor phase with ammonia and oxygen in the presence of a catalyst, the active phase of which being as described above.

Of course, in the context of the process of the invention, it is possible to use diluent gases which are inert under the reaction conditions, such as helium, nitrogen and argon. Likewise, steam can be added to the gaseous reaction mixture over wide limits. The reactive gas (saturated hydrocarbon, ammonia, oxygen) can thus be diluted with an inert diluent and/or with steam. In this mixture, the content of steam can vary over wide limits, in particular from 0% to 50% and, preferably, from 3% to 30%. In another preferred embodiment of the invention, for good results the content of reaction gas will be at least 3% and preferably at least 20%.

Within the reactive gas, the respective contents of saturated hydrocarbon, ammonia and oxygen can also vary over wide limits.

The content of saturated hydrocarbon in the reactive gas preferably ranges from 5% to 70%. That of ammonia preferably ranges from 3% to 50% and that of oxygen preferably ranges from 3% to 45%.

Figure 1:
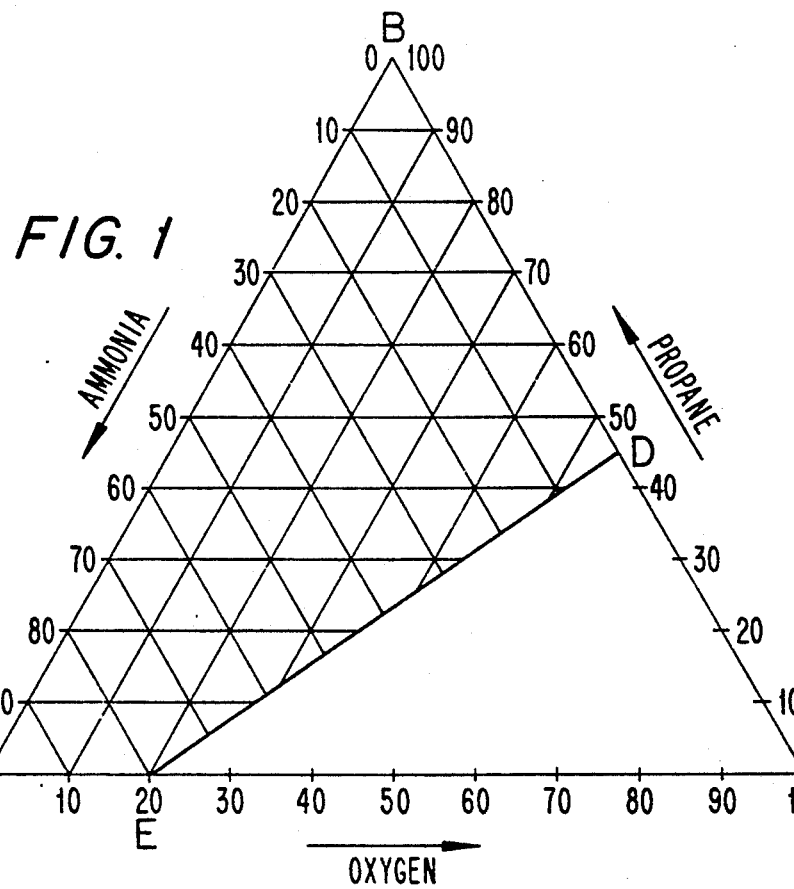
FIG. 1 is a ternary diagram indicating preferred compositions of certain gaseous feedstreams subjected to ammoxidation/conversion according to this invention.

Also for good results, the composition of the reaction mixture will be outside the explosive region. Regarding the ammoxidation of propane in the absence of inert diluent, the composition (propane, oxygen, ammonia) will advantageously be selected from within the quadrilateral ABDE which appears in the ternary diagram ABC shown in the accompanying FIG. 1.

In this ternary diagram, segment AB represents the ammonia content from 100% to 0%; segment BC represents the propane content from 100% to 0%; segment CA represents the oxygen content from 100% to 0%. Point D, situated on segment BC, corresponds to a propane content of 45% in the binary system (propane/$O_2$); point E, situated on segment AC, corresponds to an ammonia content of 79% in the binary system (ammonia/$O_2$).

Segment DE divides the ternary diagram into two parts: a triangle CDE within which is situated the explosive region (determined at 1 bar and at 25° C.) and a quadrilateral ABDE within which the composition of the reactive gaseous mixture will advantageously be selected.

Regarding the ammoxidation of propane in the presence of inert diluent gas(es) and/or of steam, it is advisable to determine the composition of the ternary mixture (propane, oxygen and ammonia) in order to situate it in the above-mentioned diagram, when the diluent gas and/or the steam is in low proportion.

Figure 2:
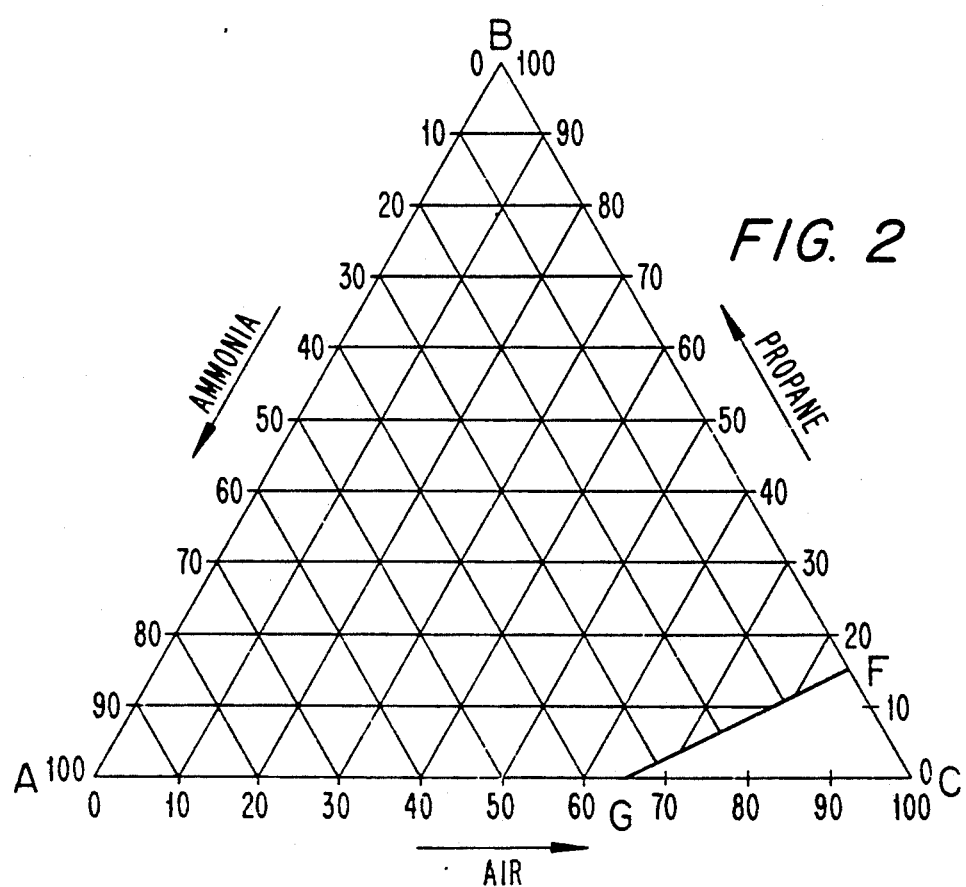
FIG. 2 is a ternary diagram indicating preferred compositions of certain other gaseous feedstreams subjected to ammoxidation/conversion according to the invention.

Regarding the ammoxidation of propane by means of air as the oxygen source, the composition (propane, air and ammonia) will advantageously be selected within the quadrilateral ABFG which appears within diagram ABC shown in the accompanying FIG. 2.

In this second diagram, segment AB represents the ammonia content from 100% to 0%; segment BC represents the propane content from 100% to 0%; segment CA represents the air content from 100% to 0%. Point F, situated on segment BC, corresponds to a propane content of 16% in the binary system (propane/air); point G, situated on segment AC, corresponds to an ammonia content of 35% in the binary system (ammonia/air).

Segment FG divides the ternary diagram into two parts; a triangle CFG within which is situated the explosive region (determined at 1 bar and at 550° C.) and a quadrilateral ABFG within the composition of the reactive gaseous mixture will advantageously be selected.

This second diagram will be used in the event that the oxygen/diluent ga mixture corresponds to an oxygen content equivalent to that of the air ($\approx 21\%$ oxygen) or in the event that this mixture is deficient in oxygen with respect to the air.

Starting from propane, a mixture will be obtained containing essentially propylene and acrylonitrile. Acrylonitrile is an intermediate produced industrially on a vast scale; propylene is a starting material traditionally used to produce acrylonitrile and various other intermediate compounds well known to this art.

Starting from isobutane, a mixture will be obtained containing methacrylonitrile and isobutene or n-butenes.

The process according to the invention is more particularly suitable for the ammoxidation of propane.

If the saturated hydrocarbon used can be of technical grade, it will not contain significant amounts of ethylenically unsaturated compounds. Thus, the starting material propane will only contain trace amounts of propylene.

The process according to the invention is carried out as a vapor phase reaction. Consequently, any apparatus suitable for carrying out ammoxidation or oxidation reactions in the vapor phase can be used. The process can be carried out continuously or noncontinuously and it can comprise the use of a stationary bed or a fluidized bed.

The reaction temperature advantageously ranges from 300° C. to 550° C. and, preferably, from 350° C. to 500° C.

The total pressure of the reaction mixture can be greater than or equal to atmospheric pressure. It advantageously ranges from 1 to 6 bar and, preferably, from 1 to 4 bar.

The gas flow rate is advantageously fixed such that the hourly volume rate ranges from 100 to 36,000 $h^{-1}$ and, preferably, from 200 to 20,000 $h^{-1}$.

The hourly volume rate is defined as the ratio total gas volume/volume of the catalyst/hour.

Of course, those skilled in the art will be able to determine a compromise between the temperature, the gas flow rate, the precise nature of the catalyst used and the various other parameters of the reaction taking account of the production objectives.

In the process according to the invention, the catalyst can be prepared or used in the following manner:

An active phase comprising a mixed oxide containing the elements V, Sb and Fe and/or Ga and/or In is first synthesized.

This active phase can optionally be deposited onto an inorganic oxide or mixed with said inorganic oxide, per se known to this art, such as, for example, alumina, silica, silica/alumina, zirconia, cerite, magnesia, titanium dioxide or niobium oxide, utilizing various techniques also per se known to this art, such as impregnation or deposition by "slurry" technique.

The catalytic phase, namely, the active phase alone or of the active phase deposited onto an inorganic oxide or mixed with said inorganic oxide, can then be used in the bulk form or in the particulate state; it can thus be used in powder form or can be shaped into the form of, for example, beads, pellets, extrudates or crushed particles, according to various known techniques.

To carry out the process in a stationary bed, these techniques can be, for example, pelleting or coating on an inert support or on a ceramic or metal substrate of monolithic type.

To carry out the process in a moving bed or in a fluidized bed, the catalytic phase is generally formed by spraying, drying and calcination.

The catalytic phase thus formed, or existing in the powder form, constitutes the catalyst according to the invention.

When the catalytic phase comprises the active phase deposited onto an inorganic oxide or mixed with said inorganic oxide, one technique for the preparation thereof can entail, in a single stage, synthesizing the active phase and depositing it onto the inorganic oxide or mixing it with said inorganic oxide.

In the description that follows, the synthesis of the active phase and its deposition onto the inorganic oxide or its admixture with the inorganic oxide will be first described separately, but the description will also apply to the variation of synthesis of the active phase in the presence of the inorganic oxide.

The preparation of the active phase employed in the process according to the invention can be carried out by various known techniques, such as mixing of suitable salts or oxides of the various elements in water or in another solvent, followed by evaporation to dryness, or by precipitation by addition of a base such as aqueous ammonia or of an acid such as hydrochloric acid, or spraying of a suspension obtained after mixing the suitable salts.

The most commonly employed suitable salts contain anions and cations which can, for example, be decomposed by heat during the subsequent stages.

Exemplary such suitable salts or oxides of vanadium include ammonium vanadate, vanadium oxyhalides such as $VOCl_3$, $VOCl_2$, $(VO_2)Cl$, $VOCl$, $VOBr$, $VOBr_2$, $VOBr_3$, $VOF_3$ and $VOF_2$, vanadium halides such as $VF_3$, $VBr_3$, $VCl_2$, $VCl_3$, $VCl_4$, $VF_5$, $VF_4$, $VBr_2$ and $VI_2$, vanadyl sulfate, vanadyl acetylacetonate, meta-vanadic acid, hexacarbonylvanadium, vanadyl triisopropoxide, and vanadium oxides such as $V_2O_5$, $V_7O_{13}$, $VO$, $VO_2$, $V_2O_3$ and $V_3O_7$.

Exemplary suitable salts or oxides of antimony include antimony oxychloride, antimony halides such as $SbBr_3$, $SbCl_3$, $SbF_3$, $SbI_3$, $SbCl_5$, $SbF_5$ and $SbI_5$, antimony sulfate, antimony acetate, antimony tartrate, antimony ethoxide, antimony butoxide, the ethylene glycol derivative of antimony, antimony oxysulfate, or antimony oxides such as $Sb_2O_3$, $Sb_2O_4$ or $Sb_2O_5$.

Exemplary suitable salts or oxides of iron includes iron nitrate, iron perchlorate, iron oxychloride, iron halides such as $FeCl_3$, $FeCl_2$, $FeBr_3$, $FeBr_2$, $FeF_3$, $FeF_2$ and $FeI_2$, iron phosphate, iron sulfate, iron iodate, pentacarbonyl-iron, iron acetate, iron acetylacetonate, iron citrate, iron formate, iron gluconate, iron glycerophosphate, iron lactate, iron malate, iron methoxide, iron oleate, iron oxalate, iron tartrate, iron 2-ethylhexanoate, or iron oxides such as $Fe_2O_3$, $Fe_3O_4$ or $FeO$.

Exemplary suitable salts or oxides of gallium include gallium nitrate, gallium perchlorate, gallium oxychloride, gallium halides such as $GaCl_3$, $GaCl_2$, $GaBr_3$, $GaF_3$ or $GaI_3$, gallium sulfate, gallium acetate, gallium acetylacetonate, gallium oxalate, or gallium oxides such as $Ga_2O_3$ or $Ga_2O$.

And exemplary suitable salts or oxides of indium include indium nitrate, indium perchlorate, indium halides such as $InCl_3$, $InCl_2$, $InCl$, $InBr_3$, $InBr_2$, $InBr$, $InF_3$, $InI_2$ or $InI$, indium phosphate, indium sulfate, indium iodate, indium acetate, indium acetylacetonate, indium methoxide, or indium oxides such as $In_2O_3$, $In_2O$ or $InO$.

The active phase is generally synthesized by the so-called evaporation method, in the following manner: an aqueous suspension of the suitable salts or oxides is prepared and the suspension is evaporated by heating to a temperature ranging from 20° to 100° C. until a viscous paste is obtained, which is dried. The precursor thus obtained can then be ground and calcined at a temperature of from 200° to 1,000° C. The active phase thus obtained can then, after cooling, be ground such that its particle size does not exceed approximately 400 μm.

The precursor can also be prepared by precipitation with addition, for example, of aqueous ammonia or of hydrochloric acid, during or at the end of mixing of the salts or oxides. It is preferable to heat the suspension at from 20° to 100° C. to drive the precipitation of the species to completion.

The suspension obtained can be evaporated under the conditions described above, or filtered and washed. The paste or filter cake, which are obtained, respectively, by evaporation or by filtration, are then dried, ground and calcined under the conditions described above in respect of the evaporation technique to provide the active phase.

This active phase can optionally be deposited onto one or more inorganic oxides or can be mixed with the inorganic oxide(s) which are known per se to this art. Exemplary of the inorganic oxides suitable for the preparation of the catalyst of the invention are alumina, silica, silica/alumina, zirconia, cerite, magnesia, titanium dioxide or niobium oxide.

The deposition onto these oxides or the mixing with these inorganic oxides can be carried out by various known techniques, such as, for example, impregnation or "slurry" deposition.

The quantity of active phase, which can vary over wide limits, as a practical matter ranges from 5% to 100% and preferably from 10% to 50% by weight with respect to the combined active phase+inorganic oxide.

Another such technique entails mixing of the inorganic oxide with the suitable salts or oxides of the various elements of the active phase under the conditions described above in respect of the preparation of the active phases. Once this mixture has been formulated, the precursor can be obtained by the so-called evaporation or precipitation methods, and then the paste or the filter cake thus produced is dried, ground and calcined under the conditions described above in respect of the preparation of the active phases.

The active phase, alone or deposited onto an inorganic oxide or mixed with an inorganic oxide such as those described above, constitutes the catalytic phase.

The catalytic phases can be used in the bulk form or in the particulate state. These phases can therefore be used in the powder form, or can be shaped, for example, into the form of beads, pellets, extrudates or crushed particles, via any one of a number of known techniques.

To carry out the process in a stationary bed, exemplary techniques suitable for the preparation of the catalysts of the invention include pelleting or coating onto an inert support or onto a ceramic or metal substrate of monolithic type.

The catalytic phases according to the invention can, for example, be shaped by compression, to produce pellets. These pellets can then optionally be crushed into fragments. The precise values of the pressure, diameter and thickness of the pellets and particle size of the fragments can easily be determined, depending upon the acceptable pressure drop in the reactor.

The catalytic phases according to the invention can also be deposited onto an inert support or can be coated thereon. The nature of this support is not critical as long as it is chemically inert with respect to the reactants under the reaction conditions selected. Exemplary supports suitable for the preparation of catalysts which can be used in the process according to the invention include silica, alumina, silica/alumina, sintered clay, carborundum, magnesia, magnesium silicate and diatomaceous earth. This support is preferably nonporous and can, especially, be based on a refractory oxide in the particulate form, the most commonly employed support being clay-based. This support can for example, comprise inert, complete, solid and rough clay beads having a diameter ranging from 0.5 mm to 6 mm. The precise value of the diameter of the beads to can be selected as a function of the acceptable pressure drop in the reactor. This support can also be rendered nonporous by enamelling.

Such support can also be a ceramic substrate, said substrate preferably being in the form of an inert and rigid structure of monolithic type comprising channels or ducts. These supports are well known to this art and have been widely described in the literature. The substrates used which are shaped from ceramic materials are especially those containing, as the principal ingredient, cordierite, alumina, mullite, porcelain, and the carbides of boron or silicon.

This support can also be a metal substrate. Such supports are also well known to this art. Suitable metal substrates are especially those produced from alloys of iron, nickel and chromium, or those produced from alloys of iron, chromium, aluminum and cobalt, such as those marketed under the trademark Kanthal, or those produced from alloys of iron, chromium, aluminum and yttrium marketed under the trademark Fercralloy. The metal can also be carbon steel or simple cast iron.

When a coated catalyst is used, the amount of catalytic phase, which can vary over wide limits, typically ranges from 1% to 50% and preferably from 3% to 35% by weight with respect to the combined support +catalytic phase.

Thus, certain catalysts, useful for carrying out the process in a stationary bed, can be prepared by coating ground, intermediate or finished, catalytic phases in a manner known per se. This conventional method entails depositing a layer of intermediate or finished catalytic phase around inert but rough beads. Once the beads are covered with the desired amount of the catalytic phase, they are dried with hot air at a temperature of from 70° to 150° C. for at least 30 minutes and then introduced into an oven to be calcined at from 300° to 600°, preferably at from 450° to 500° C., for at least 3 hours.

Certain catalysts which are useful for carrying out the process according to the invention in a moving bed or fluidized bed can be produced by the technique, also known per se, of drying by spraying in a preferably nonreducing atmosphere. By such an operation, followed if appropriate by calcination at a temperature on the order of 400° to 1,100° C., powders are obtained which are spherical in shape and have a diameter ranging from 5 to 700 $\mu$m. Powders comprising at least 80% by weight of particles having sizes ranging from 5 to 200 $\mu$m are preferred when the subject process is carried out in a fluidized bed.

The catalytic phase thus employed in the bulk form or the particulate state constitutes the catalyst according to the invention.

The products of the reaction can be recovered from the effluent gases by any suitable means. For example, the effluent gases can be conveyed into a condenser containing dilute sulfuric acid in order to neutralize the unreacted ammonia. The gases can then pass through a refrigerated absorbing column to condense the acrylonitrile, acetonitrile and hydrocyanic acid, the uncondensed vapors principally containing unreacted propane, propylene, light hydrocarbons and, if appropriate, $CO_2$. The acrylonitrile and hydrocyanic acid can then be separated from the acetonitrile by distillation and the recovered acrylonitrile/hydrocyanic acid mixture can in turn be distilled to separate the acrylonitrile from the hydrocyanic acid.

In order to further illustrate the present invention and the advantages thereof, the following specific examples are given, it being understood that same are intended only as illustrative and in nowise limitative.

EXAMPLE 1

Preparation of a catalyst ($A_1$) according to the invention having the empirical formula (II), $VSb_{3.5}Fe_2O_x$/$Al_2O_3$ (25/75% by weight) (II):

(A) A solution (a) of ammonium vanadate was prepared by dissolving 2.34 g of $NH_4VO_3$ in 400 cm$^3$ of demineralized water, a solution (b) of iron nitrate was prepared by dissolving 16.2 g of $Fe(NO_3)_3 \cdot 9H_2O$ in 70 cm$^3$ of demineralized water and a suspension (c) of antimony chloride was prepared by dissolving 10.2 g of $Sb_2O_3$ in 250 cm$^3$ of 1N hydrochloric acid. Solution (b) was added to solution (a) with stirring at approximately 70° C. and then suspension (c) was added. 47.3 g of $Al_2O_3$ were then added at approximately 90° C. The mixture was maintained at 90° C. for 6 hours, evaporated to dryness, and the residue was dried at 120° C. for approximately 15 hours and then calcined at 550° C. for 10 hours.

(B) The product of formula (II) thus obtained was then compressed under a pressure of 4,300 kg/cm$^2$. Pellets were thus obtained having a diameter of 3 cm and a thickness of approximately 0.5 cm. These pellets were crushed into fragments having a particle size ranging from 0.3 to 0.8 cm constituting the catalyst $A_1$ in accordance with the invention.

EXAMPLE 2

Preparation of a catalyst ($A_2$) according to the invention having the empirical formula $VSb_{3.5}Fe_2O_x$/$Al_2O_3$ (25/75% by weight) coated onto clay beads:

The product of formula (II) obtained in stage (A) of Example 1 was employed in the following manner:

15 g of the said product prepared above were slowly dusted over 100 g of inert support composed of clay beads having a mean diameter of 4.8 mm, placed beforehand in a rotary coating device and moistened with 10% aqueous glucose solution; as soon as the beads were dry on the outside, a small amount of the glucose solution was sprayed thereon. The product of formula (II) was then again dusted onto the beads. These operations were continued alternately until all of the product of formula (II) had been coated onto the beads.

Drying was then carried out at 120° C. for 2 hours and calcination was carried out for 6 hours at 480° C.

The catalyst $A_2$ thus obtained contained 10.4% by weight of $VSb_{3.5}Fe_2O_x/Al_2O_3$ (25/75% by weight) coated onto clay beads.

EXAMPLE 3

Preparation of a catalyst ($B_1$) according to the invention having the empirical formula (III), $VSb_{3.5}Ga_2O_x/Al_2O_3$ (25/75% by weight):

(A) The product of formula (III) $VSb_{3.5}Ga_2O_x/Al_2O_3$ was prepared in the following manner: a solution (a) of ammonium vanadate was prepared by dissolving 2.34 g of $NH_4VO_3$ in 400 cm$^3$ of demineralized water, a solution (b) of gallium nitrate was prepared by dissolving 10.2 g of $Ga(NO_3)_3$ in 50 cm$^3$ of demineralized water and a suspension (c) of antimony chloride was prepared by dissolving 10.2 g of $Sb_2O_3$ in 250 cm$^3$ of 1N hydrochloric acid. Solution (b) was added to solution (a) with stirring at approximately 80° C., and then suspension (c) was added. 47.3 g of $Al_2O_3$ were then added at approximately 90° C. The mixture was heated at 105° C. for 6 hours and evaporated to dryness, and the residue was dried at 120° C. for approximately 15 hours and then calcined at 550° C. for 10 hours.

(B) The product of formula III thus prepared in (A) was then compressed under a pressure of 4,300 kg/cm$^2$. Pellets were thus obtained having a diameter of 3 cm and a thickness of approximately 0.5 cm. These pellets were then crushed into fragments having a particle size ranging from 0.3 cm to 0.8 cm constituting the catalyst $B_1$ in accordance with the invention.

EXAMPLE 4

Preparation of a catalyst ($B_2$) according to the invention having the empirical formula $VSb_{3.5}Ga_2O_x/Al_2O_3$ (25/75% by weight) coated onto clay beads:

The product of formula (III) obtained in stage (A) of Example 3 was employed in the following manner:

15 g of the product of formula (III) thus prepared were slowly dusted over 100 g of inert support composed of clay beads having a mean diameter of 4.8 mm, placed beforehand in a rotary coating device and moistened with 10% aqueous glucose solution. As soon as the beads were dry on the outside, a small amount of the glucose solution was sprayed thereon. The product of formula (III) was then again dusted onto the beads. These operations were continued alternately until all of the said product had been coated onto the beads. Drying was then carried out at 120° C. for 2 hours and calcining at 480° C. for 6 hours.

The catalyst ($B_2$) thus obtained, in accordance with the invention, contained 4.3% by weight of $VSb_{3.5}Ga_2O_x/Al_2O_3$ (25/75% by weight) coated onto the clay beads.

EXAMPLE 5

Preparation of a catalyst (C) according to the invention having the empirical formula (IV), $VSb_{3.5}In_2O_x/Al_2O_3$ (25/75% by weight) (IV):

(A) A solution (a) of ammonium vanadate was prepared by dissolving 1.5 g of $NH_4VO_3$ in 250 cm$^3$ of demineralized water, a suspension (b) of antimony chloride was prepared by dissolving 6.53 g of $Sb_2O_3$ in 13.4 cm$^3$ of 37% hydrochloric acid and 150 cm$^3$ of demineralized water, and a solution (c) of indium nitrate was prepared by dissolving 10 g of $In(NO_3)_3.5H_2O$ in 50 cm$^3$ of demineralized water. Solution (c), then suspension (b) and then 30.3 g of $Al_2O_3$ were added to solution (a) with stirring at approximately 80° C. The mixture was maintained at this temperature for 6 hours and then evaporated to dryness, and the residue was dried at 120° C. for approximately 15 hours and then calcined at 550° C. for 10 hours.

(B) The product of formula (IV) thus obtained was then compressed under a pressure of 4,300 kg/cm$^2$. Pellets were thus obtained having a diameter of 3 cm and a thickness of approximately 0.5 cm. These pellets were then crushed into fragments having a particle size ranging from 0.3 to 0.8 cm constituting the catalyst C in accordance with the invention.

EXAMPLE 6

Preparation of a catalyst (D) according to the invention having the empirical formula (V), $VSb_5Fe_2O_x/Al_2O_3$ (25/75% by weight) (V):

(A) A solution (a) of ammonium vanadate was prepared by dissolving 2.34 g of $NH_4VO_3$ in 400 cm$_3$ of demineralized water, a solution (b) of iron nitrate was prepared by dissolving 16.2 g of $Fe(NO_3)_3.9H_2O$ in 70 cm$^3$ of demineralized water and a suspension (c) of antimony chloride was prepared by dissolving 14.6 g of $Sb_2O_3$ in 30 cm$^3$ of 37% hydrochloric acid and 300 cm$^3$ of demineralized water. Solution (b) was added to solution (a) with stirring at approximately 70° C., and then suspension (c) was added. The mixture was heated to reflux and 47.3 g of $Al_2O_3$ were added. The mixture was maintained at this temperature for 6 hours and evaporated to dryness, and the residue was dried at 120° C. for approximately 15 hours and then calcined at 550° C. for 10 hours.

(B) The product of formula (V) thus obtained was then compressed under a pressure of 4,300 kg /cm$^2$. Pellets were thus obtained having a diameter of 3 cm and a thickness of approximately 0.5 cm. These pellets were then crushed into fragments having a particle size ranging from 0.3 to 0.8 cm constituting the catalyst D in accordance with the invention.

COMPARATIVE EXAMPLE 1

Preparation of a catalyst (E) not according to the invention, having the empirical formula: $VSb_{3.5}Fe_{0.1}O_x/Al_2O_3$ (25/75% by weight):

A product having the composition $VSb_{3.5}Fe_{0.1}O_x/Al_2O_3$ (25/75% by weight) was prepared according to the following procedure:

A solution (a) of ammonium vanadate was prepared by dissolving 2.34 g of $NH_4VO_3$ in 400 cm$^3$ of demineralized water, a solution (b) of iron nitrate was prepared by dissolving 0.81 g of $Fe(NO_3)_3.9H_2O$ in 70 cm$^3$ of demineralized water and a suspension (c) of antimony chloride was prepared by dissolving 10.2 g of $Sb_2O_3$ in 21 cm$^3$ of 37% hydrochloric acid and 250 cm$^3$ of demineralized water. Solution (b) was added to solution (a) with stirring at approximately 70° C. and then suspension (c) was added. The mixture was heated to reflux and 47.3 g of $Al_2O_3$ were added. The mixture was maintained at this temperature for 6 hours, was evaporated to dryness, and the residue was dried at 120° C. for approximately 15 hours and was then calcined at 550° C. for 10 hours.

This product was then compressed under a pressure of 4,300 kg/cm$^3$. Pellets were thus obtained having a diameter of 3 cm and a thickness of approximately 0.5 cm. These pellets were then crushed into fragments having a particle size ranging from 0.3 to 0.8 cm, constituting the catalyst (E), of composition VSb$_{3.5}$Fe$_{0.1}$O$_x$/Al$_2$O$_3$ (25/75% by weight) but not according to the invention.

COMPARATIVE EXAMPLE 2

Preparation of a catalyst (F) not according to the invention, having the empirical formula: VSb$_{3.5}$O$_x$/Al$_2$O$_3$ (25/75% by weight):

A product having the composition VSb$_{3.5}$O$_x$/Al$_2$O$_3$ (25/75% by weight) was prepared according to the following procedure:

A solution (a) of ammonium vanadate was prepared by dissolving 2.34 g of NH$_4$VO$_3$ in 400 cm$^3$ of demineralized water and a suspension (b) of antimony chloride was prepared by dissolving 10.2 g of Sb$_2$O$_3$ in 21 cm$^3$ of 37% hydrochloric acid and 230 cm$^3$ of demineralized water. Suspension (b), and then 47.3 g of Al$_2$O$_3$, were added to suspension (a) with stirring at approximately 80°–90° C. The mixture was maintained at this temperature for 6 hours, evaporated to dryness, and the residue was dried at 120° C. for approximately 15 hours and then calcined at 550° C. for 10 hours.

This product was then compressed under a pressure of 4,300 kg/cm$^2$. Pellets were thus obtained having a diameter of 3 cm and a thickness of approximately 0.5 cm. These pellets were then crushed into fragments having a particle size ranging from 0.3 to 0.8 cm, constituting the catalyst (F), of composition VSb$_{3.5}$O$_x$/Al$_2$O$_3$ (25/75% by weight), but not according to the invention.

GENERAL PROCEDURE FOR THE AMMOXIDATION TESTS

The catalyst sample was heated beforehand to a temperature of 150° C. on a test bench while purging with helium for 10 min, and it was then subjected to a gas flow whose composition will be specified for each Example and which contained propane, ammonia, oxygen, steam and helium.

The total pressure of the reaction mixture, ranging from 1 to 6 bar, will also be specified for each Example.

The total gas flow rate is defined such as to provide a hourly volume rate (HVR) ranging from 100 to 36,000 h$^{-1}$, the precise value of which will be indicated for each Example.

Catalyst volume:
(catalytic phase + optional support): 25 cm$^3$.

When the volume of the catalyst used will be different from this value, the specific value will be indicated in the Examples.

The principle of the ammoxidation test for propane was the following:

(i) The catalyst was heated to a temperature T$_1$, for example 300° C., and, after stabilizing for 30 min at the temperature T$_1$, the composition of the mixture of the reactor outlet was determined by gas phase chromatography.

(ii) The conversion percentages and the selectivities obtained on the catalyst examined at the inlet temperature T$_1$ were calculated using relationships of the type:

(1) conversion of propane (% in moles) = converted propane/introduced propane (2) selectivity for acrylonitrile (% in moles) = propane converted to acrylonitrile/converted propane (iii) The catalyst was then heated from 300° to 550° C. by increments of 20° C. and the conversion percentages and the selectivities were determined every 40 min.

In the Examples below, the following conventions are used:

| | |
|---|---|
| DC(C$_3$H$_8$) = | conversion of propane, |
| S(ACN) = | selectivity for acrylonitrile, |
| S(ACN + C$_3$H$_6$) = | selectivity for acrylonitrile and propylene, |
| S(CO$_x$) = | selectivity for carbon monoxide and carbon dioxide, |
| S(Ammox) = | selectivity for acetonitrile, hydrocyanic acid and other (amm)oxidation byproducts, |
| S(C$_1$-C$_2$) = | selectivity for methane, ethane and ethylene. |

EXAMPLE 7 AND COMPARATIVE EXAMPLE 3

Measurement of the performances of the catalysts (A$_1$) and (E).

The operating conditions employed were the following:

| | |
|---|---|
| Hourly volume rate = | 1,000 h$^{-1}$ |
| Total pressure = | 1.3 bar |

Composition by volume of the reaction mixture:

| | |
|---|---|
| CH$_3$H$_8$ = | 48% |
| NH$_3$ = | 9% |
| O$_2$ = | 18% |
| H$_2$O = | 20% |
| He = | 5% |

The temperature conditions and the results obtained are reported in Table 1 below:

TABLE 1

| Tests | Example 7 | | | | Comprative Example 3 | | | |
|---|---|---|---|---|---|---|---|---|
| Catalyst used | A$_1$ | | | | E | | | |
| Temperature (in °C.) | 380 | 400 | 420 | 440 | 380 | 400 | 410 | 430 |
| DC(C$_3$H$_8$) % | 9.5 | 12 | 11 | 10 | 7 | 12 | 13 | 19 |
| S(ACN) % | 34 | 36 | 38 | 33 | 2 | 10 | 8 | 17 |
| S(ACN + C$_3$H$_6$) % | 68 | 63 | 71 | 76 | 49 | 42 | 41 | 41 |
| S(Ammox) % | 39 | 36 | 26 | 19 | 22 | 44 | 44 | 54 |
| S(C$_1$-C$_2$) % | 0 | 0 | 0 | 1 | 0 | 0 | 0 | 0 |
| S(CO$_x$) % | 0 | 0 | 2 | 4 | 29 | 14 | 15 | 5 |

EXAMPLE 8 AND COMPARATIVE EXAMPLE 4

Measurement of the performances of the catalysts (A$_1$) and (E).

The operating conditions employed were the following:

| | |
|---|---|
| Hourly volume rate = | 1,000 h$^{-1}$ |
| Total pressure = | 1.3 bar |

Composition by volume of the reaction mixture:

| | |
|---|---|
| $C_3H_8$ = | 7.5% |
| $NH_3$ = | 15% |
| $O_2$ = | 15% |
| $H_2O$ = | 20% |
| He = | 42.5% |

The temperature conditions and the results obtained are reported in Table 2 below:

TABLE 2

| Tests | Example 8 | | | | | Comprative Example 4 | | | | |
|---|---|---|---|---|---|---|---|---|---|---|
| Catalyst used | $A_1$ | | | | | E | | | | |
| Temperature (in °C.) | 380 | 400 | 420 | 440 | 460 | 380 | 400 | 420 | 440 | 460 |
| $DC(C_3H_8)$ % | 2 | 5 | 15 | 31 | 38 | 4 | 8 | 15 | 26 | 42 |
| S(ACN) % | 18 | 34 | 66 | 74 | 66 | 9 | 18 | 31 | 27 | 34 |
| $S(ACN + C_3H_6)$ % | 79 | 65 | 78 | 81 | 75 | 44 | 44 | 50 | 39 | 43 |
| S(Ammox) % | 17 | 33 | 18 | 18 | 10 | 56 | 50 | 41 | 38 | 40 |
| $S(C_1-C_2)$ % | 0 | 0 | 4 | 0 | 0 | 0 | 0 | 0 | 0 | 0 |
| $S(CO_x)$ % | 4 | 2 | 0 | 0 | 15 | 0 | 7 | 10 | 22 | 17 |

EXAMPLES 9 AND 10

Measurement of the performance of the catalyst ($B_2$).
The operating conditions employed were the following:

| | |
|---|---|
| Hourly volume rate = | 1,000 h$^{-1}$ |
| Total pressure = | 1.3 bar |

The composition by volume of the reaction mixture, the temperature conditions (T(°C.)) and the results obtained are reported in Table 3 below:

TABLE 3

| Examples | $C_3H_8$ (%) | $NH_3$ (%) | $O_2$ (%) | $H_2O$ (%) | He (%) | T (°C.) | DC ($C_3H_8$) (%) | S(ACN) (%) | S(ACN + $C_3H_6$) | S(Ammox) (%) | $S(C_1-C_2)$ (%) | $S(CO_x)$ (%) |
|---|---|---|---|---|---|---|---|---|---|---|---|---|
| Example 9 | 7.5 | 15 | 15 | 20 | 42.5 | 500 | 12.5 | 10 | 61 | 28 | 9 | 1 |
| Example 10 | 25 | 10 | 25 | 20 | 20 | 480 | 6 | 10 | 68 | 27 | 4 | 0 |

EXAMPLE 11

Measurement of the performance of the catalyst ($A_2$).
The operating conditions employed were the following:

| | |
|---|---|
| Hourly volume rate = | 1,000 h$^{-1}$ |
| Total pressure = | 1.3 bar |

Composition by volume of the reaction mixture:

| | |
|---|---|
| $C_3H_8$ = | 48% |
| $NH_3$ = | 9% |
| $O_2$ = | 18% |
| $H_2O$ = | 20% |
| He | 5% |

The temperature conditions and the results obtained are reported in Table 4 below:

TABLE 4

| | 460° C. | 480° C. | 480° C. |
|---|---|---|---|
| $DC(C_3H_8)$ % | 2 | 5 | 8.5 |
| S(ACN) | 15 | 38 | 46 |
| $S(ACN + C_3H_6)$ % | 86 | 86 | 82 |
| S(Ammox) % | 6 | 11 | 15 |
| $S(C_1-C_2)$ % | 8 | 3 | 3 |
| $S(CO_x)$ % | 0 | 0 | 0 |

EXAMPLES 12 AND 13

Measurement of the performances of the catalysts ($B_1$) and (C).
The operating conditions employed were the following:

| | |
|---|---|
| Hourly volume rate = | 1,000 h$^{-1}$ |
| Total pressure = | 1.3 bar |

Composition by volume of the reaction mixture:

| | |
|---|---|
| $C_3H_8$ = | 7.5% |
| $NH_3$ = | 15% |
| $O_2$ = | 15% |
| $H_2O$ = | 20% |
| He = | 42.5% |

The temperature conditions and the results obtained are reported in Table 5 below:

TABLE 5

| Examples | Example 12 | | | | Comprative Example 13 | | | |
|---|---|---|---|---|---|---|---|---|
| Catalyst used | $B_1$ | | | | C | | | |
| Temperature (in °C.) | 400 | 420 | 440 | 460 | 380 | 400 | 420 | 440 |
| $DC(C_3H_8)$ % | 14 | 29 | 43 | 49 | 5 | 11 | 23 | 32 |
| S(ACN) % | 21 | 36 | 48 | 56 | 12 | 31 | 56 | 56 |
| $S(ACN + C_3H_6)$ % | 39 | 46 | 57 | 66 | 61 | 57 | 71 | 69 |
| S(Ammox) % | 58 | 43 | 37 | 26 | 39 | 37 | 25 | 17 |
| $S(C_1-C_2)$ % | 0 | 0 | 0 | 0 | 0 | 0 | 4 | 1 |
| $S(CO_x)$ % | 3 | 11 | 7 | 8 | 0 | 5 | 0 | 14 |

EXAMPLE 14 AND COMPARATIVE EXAMPLE 5

Measurement of the performances of the catalysts (C) and (F).
The operating conditions employed were the following:

| Hourly volume rate = | 1,000 h$^{-1}$ |
|---|---|
| Total pressure = | 1.3 bar |

Composition by volume of the reaction mixture:

| C$_3$H$_8$ = | 40% |
|---|---|
| NH$_3$ = | 15% |
| O$_2$ = | 15% |
| H$_2$O = | 20% |
| He = | 10% |

The temperature conditions and the results obtained are reported in Table 6 below:

TABLE 6

| Tests | Example 14 | | | | Comparative Example 5 | | | |
|---|---|---|---|---|---|---|---|---|
| Catalyst used | C | | | | F | | | |
| Temperature (in °C.) | 400 | 420 | 440 | 460 | 400 | 420 | 440 | 460 |
| DC(C$_3$H$_8$) % | 7 | 11 | 11 | 12 | 15 | 15 | 15 | 17 |
| S(ACN) % | 33 | 35 | 39 | 36 | 28 | 21 | 16 | 14 |
| S(ACN + C$_3$H$_6$) % | 74 | 68 | 71 | 70 | 68 | 64 | 63 | 62 |
| S(Ammox) % | 21 | 23 | 20 | 19 | 26 | 28 | 26 | 23 |
| S(C$_1$-C$_2$) % | 0.5 | 1 | 2 | 4 | 0.5 | 0 | 1 | 5 |
| S(CO$_x$) % | 4 | 8 | 7 | 7 | 6 | 8 | 11 | 10 |

EXAMPLE 15

Measurement of the performance of the catalyst (C). The operating conditions employed were the following:

| Hourly volume rate = | 1,000 h$^{-1}$ |
|---|---|
| Total pressure = | 1.3 bar |

Composition by volume of the reaction mixture.

| C$_3$H$_8$ = | 25% |
|---|---|
| NH$_3$ = | 25% |
| O$_2$ = | 10% |
| H$_2$O = | 20% |
| He = | 20% |

The temperature conditions and the results obtained are reported in Table 7 below:

TABLE 7

| Temperature | 400(°C.) | 420(°C.) | 440(°C.) | 460(°C.) | 480(°C.) |
|---|---|---|---|---|---|
| DC | 7 | 13 | 13 | 13 | 13 |
| S(ACN) | 34 | 32 | 37 | 42 | 46 |
| S(ACN + C$_3$H$_6$) % | 70 | 59 | 63 | 68 | 74 |
| S(Ammox) % | 30 | 40 | 30 | 26 | 19 |
| S(C$_1$-C$_2$) % | 0 | 0 | 7 | 6 | 7 |
| S(CO$_x$) % | 0 | 0 | 0 | 0 | 0 |

EXAMPLE 16

Measurement of the performance of the catalyst (A$_1$).

The operating conditions employed were the following:

| Hourly volume rate = | 1,000 h$^{-1}$ |
|---|---|
| Total pressure = | 1.3 bar |
| Volume of the catalyst: | 19 cm$^3$ |

Composition by volume of the reaction mixture:

| C$_3$H$_8$ = | 25% |
|---|---|
| NH$_3$ = | 25% |
| O$_2$ = | 10% |
| H$_2$O = | 20% |
| He = | 20% |

The temperature conditions and the results obtained are reported in Table 8 below:

TABLE 8

| Temperature | 380(°C.) | 400(°C.) | 420(°C.) | 440(°C.) | 480(°C.) |
|---|---|---|---|---|---|
| DC(C$_3$H$_8$) % | 3 | 7 | 10 | 10 | 11 |
| S(ACN) % | 30 | 51 | 52 | 45 | 44 |
| S(ACN + C$_3$H$_6$) % | 78 | 82 | 85 | 85 | 85 |
| S(Ammox) % | 23 | 19 | 15 | 15 | 15 |
| S(C$_1$-C$_2$) % | 0 | 0 | 0 | 0 | 0 |
| S(CO$_x$) % | 0 | 0 | 0 | 0 | 0 |

EXAMPLE 17

Measurement of the performance of the catalyst (D). The operating conditions employed were the following:

| Hourly volume rate = | 1,000 h$^{-1}$ |
|---|---|
| Total pressure = | 1.3 bar |

Composition by volume of the reaction mixture:

| C$_3$H$_8$ = | 7.5% |
|---|---|
| NH$_3$ = | 15% |
| O$_2$ = | 15% |
| H$_2$O = | 20% |
| He = | 42.5% |

The temperature conditions and the results obtained are reported in Table 9 below:

TABLE 9

| Temperature (in °C.) | 360 | 380 | 400 | 420 | 440 | 460 |
|---|---|---|---|---|---|---|
| DC(C$_3$H$_8$) % | 3 | 9 | 12 | 23 | 34 | 45 |
| S(ACN) % | 16 | 41 | 60 | 72 | 76 | 76 |
| S(ACN + C$_3$H$_6$) % | 32 | 48 | 68 | 77 | 79 | 80 |
| S(Ammox) % | 68 | 53 | 31 | 19 | 13 | 12 |
| S(C$_1$-C$_2$) % | 0 | 0 | 0 | 0 | 0 | 0 |
| S(CO$_x$) % | 0 | 0 | 1 | 5 | 8 | 8 |

EXAMPLE 18

Measurement of the performances of the catalysts (D).

The operating conditions employed were the following:

| Hourly volume rate = | 1,000 h$^{-1}$ |
|---|---|
| Total pressure = | 1.3 bar |

Composition by volume of the reaction mixture:

| C$_3$H$_8$ = | 20% |
|---|---|
| NH$_3$ = | 20% |
| O$_2$ = | 20% |
| H$_2$O = | 20% |
| He = | 20% |

The temperature conditions and the results obtained are reported in Table 10 below:

TABLE 10

| Temperature | 370(°C.) | 380(°C.) | 390(°C.) | 400(°C.) |
|---|---|---|---|---|
| DC(C$_3$H$_8$) % | 2 | 4 | 7 | 11 |
| S(ACN) % | 18 | 28 | 43 | 56 |
| S(ACN + C$_3$H$_6$) % | 42 | 49 | 58 | 68 |
| S(Ammox) % | 58 | 51 | 42 | 32 |
| S(C$_1$-C$_2$) % | 0 | 0 | 0 | 0 |
| S(CO$_x$) % | 0 | 0 | 0 | 1 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the ammoxidation of a saturated hydrocarbon into an α,β-ethylenically unsaturated nitrile, by reacting an acyclic alkane containing at least 3 carbon atoms per molecule with ammonia and oxygen, in vapor phase, and in the presence of a catalytically effective amount of a solid catalyst, said catalyst having an active phase represented by the empirical formula (I):

VSb$_a$M$_b$O$_x$     (I)

in which a is a number equal to or greater than 1, M is iron, gallium, indium or mixtures thereof, b is a number equal to or greater than 0.5, and x is a number provided by the oxidation number of the other elements of said at least one active catalytic phase and said active catalytic phase represented by formula (I) being the sole ammoxidation component catalyst in the process.

2. A process for the ammoxidation of a saturated hydrocarbon into an α,β-ethylenically unsaturated nitrile, by reacting an acyclic alkane containing at least 3 carbon atoms per molecule with ammonia and oxygen, in vapor phase and in the presence of a catalytically effective amount of a solid catalyst, said catalyst having a single active phase represented by the empirical formula (I):

VSb$_a$M$_b$O$_x$     (I)

in which a is a whole or fractional number ranging from 1 to 10, M is iron, gallium, indium or mixtures thereof, b is a number equal to or greater than 0.5, and x is a number provided by the oxidation number of the other elements of said at least one active catalytic phase and said active catalytic phase represented by formula (I) being the sole ammoxidation component catalyst in the process.

3. The process as defined by claim 1, wherein said at least one active catalytic phase having the formula (I), a is a whole or fractional number ranging from 1 to 10, and b is a whole or fractional number ranging from 1 to 10.

4. The process as defined by claim 1, carried out at a temperature ranging from 300° to 550° C.

5. The process as defined by claim 4, carried out at a temperature ranging from 350° to 500° C.

6. The process as defined by claim 1, said alkane reactant comprising propane.

7. The process as defined by claim 1, carried out under a total pressure ranging from 1 to 6 bar.

8. The process as defined by claim 1, carried out at an hourly volume rate ranging from 100 to 36,000 h$^{-1}$.

9. The process as defined by claim 1, the gaseous mixture of reaction comprising from 5% to 70% of said alkane, from 3% to 50% of ammonia, and from 3% to 45% of oxygen.

10. The process as defined by claim 1, the composition of the gaseous mixture of reaction being outside the explosive region thereof.

11. The process as defined by claim 1, said catalyst further comprising at least one inert inorganic oxide support.

12. The process as defined by claim 11, said at least one inert inorganic oxide support comprising alumia, silica, silica/alumia, zirconia, cerite, magnesia, titanium dioxide, niobium oxide, or mixture thereof.

13. The process as defined by claim 1, said solid catalyst further comprising an inert support.

14. The process as defined by claim 1, said solid catalyst further comprising an inert ceramic or metal substrate.

15. The process as defined by claim 14, said at least one active catalytic phase comprising at least 5% by weight of said solid catalyst.

16. The process as defined by claim 13, said at least one active catalytic phase comprising from 1% to 50% by weight of said solid catalyst.

17. The process as defined by claim 14, said at least one active catalytic phase comprising from 1% to 50% by weight of said solid catalyst.

18. The process as defined by claim 15, said at least one active catalytic phase comprising from 10% to 50% by weight of said solid catalyst.

19. The process as defined by claim 1, carried out in the presence of steam or an inert diluent.

20. The process as defined by claim 1, wherein said at least one active catalytic phase having the formula (I), M is iron.

21. The process as defined by claim 1, wherein said at least one active catalytic phase having the formula (I), M is gallium.

22. The process as defined by claim 1, wherein said at least one active catalytic phase having the formula (I), M is indium.

* * * * *